United States Patent [19]

Reutelingsperger

[11] Patent Number: 5,955,437
[45] Date of Patent: Sep. 21, 1999

[54] USE OF AN ANTICOAGULANT AS A DIAGNOSTIC AGENT

[75] Inventor: Christiaan Reutelingsperger, Maastricht, Netherlands

[73] Assignee: Boehringer Ingelheim International GmbH, Ingelheim am Rhein, Germany

[21] Appl. No.: 08/445,859

[22] Filed: May 22, 1995

Related U.S. Application Data

[62] Division of application No. 08/183,788, Jan. 21, 1994, Pat. No. 5,627,036, which is a continuation of application No. 07/904,366, Jun. 26, 1992, abandoned, which is a continuation-in-part of application No. 07/862,572, filed as application No. PCT/EP90/02257, Dec. 19, 1990.

[30] Foreign Application Priority Data

Dec. 27, 1989 [DE] Germany .............................. 39 42 988

[51] Int. Cl.$^6$ ................................................. G01N 33/566
[52] U.S. Cl. ........................... 514/21; 530/345; 530/350; 530/380; 424/1.69; 424/9.3
[58] Field of Search ........................ 514/12, 21; 530/324, 530/350, 380, 345; 424/101, 1.69, 9.3

[56] References Cited

U.S. PATENT DOCUMENTS

| | | | |
|---|---|---|---|
| 3,933,996 | 1/1976 | Charlton et al. | 424/1 |
| 4,385,046 | 5/1983 | Milbrath et al. | 424/1 |
| 4,416,865 | 11/1983 | Rhodes et al. | 924/1.1 |
| 4,427,646 | 1/1984 | Olexa et al. | 424/1.1 |
| 4,455,290 | 6/1984 | Olexa et al. | 424/1.1 |
| 4,659,839 | 4/1987 | Nicolotti et al. | 548/546 |
| 4,736,018 | 4/1988 | Reutelingsperger | 530/381 |
| 4,820,505 | 4/1989 | Ginsberg et al. | 424/9 |
| 4,937,324 | 6/1990 | Fujikawa et al. | 530/397 |
| 5,066,787 | 11/1991 | Reutelingsperger | 530/380 |
| 5,066,788 | 11/1991 | Reutelingsperger | 530/381 |
| 5,118,610 | 6/1992 | Kitto | 435/7.21 |

FOREIGN PATENT DOCUMENTS

| | | |
|---|---|---|
| 0 063 002 | 10/1982 | European Pat. Off. . |
| 0 181 465 | 5/1986 | European Pat. Off. . |
| 0 279 459 | 8/1988 | European Pat. Off. . |
| 0 293 567 | 12/1988 | European Pat. Off. . |
| 0 318 703 | 6/1989 | European Pat. Off. . |
| 0 409 053 | 1/1991 | European Pat. Off. . |
| 3810331 | 10/1989 | Germany . |
| WO 88/05659 | 8/1988 | WIPO . |
| WO 91/09628 | 7/1991 | WIPO . |

OTHER PUBLICATIONS

Bevers, E.M. et al., "Changes in Membrane Phospholipid Disribution During Platelet Activation", *Biochim. Biophys. Acta* 736:57–66 (1983).

Concha et al., "Rat Annexin V Crystal Structure: $Ca^{2+}$–Induced Conformational Changes", *Science* 261:1321–1324 (Sep. 3, 1993).

Crompton, M.R. et al., "Diversity in the Lipocortin/Calpactin Family", *Cell* 55:1–3 (Oct. 7, 1988).

Funakoshi, T. et al., "Primary Structure of Human Placental Anticoagulant Protein", *Biochemistry* 26(25):8087–8092 (1987).

Geisow, M.J., "Common Domain Structure of $Ca^{2+}$ and Lipid–Binding Proteins", *FEBS Lett.* 203(1):99–103 (Jul., 1986).

Geisow, M.J. et al., "Localization and Structure of Novel Calcium–Regulated Phospholipid–Binding Proteins", *Biochem. Soc, Trans.* 25:800–802 (1987).

Hauptmann & Reutelingsperger, "Molecular Biology and Biochemistry of Annexins V and VIII", *Portland Press Res. Monogr.* 2:139–150 (1992).

Kaetzel, M.A. et al., "Differential Tissue Expression of Three 35–kDa Annexin Calcium–Dependent Phospholipid–Binding Proteins", *J. Biol. Chem.* 264(24):14463–14470 (Aug. 25, 1989).

Maurer–Fogy, I. et al., "Cloning and Expression of cDNA for Human Vascular Antiocoagulant, a $Ca^{2+}$–Dependent Phospholipid–Binding Protein", *Eur. J. Biochem.* 174(4):585–592 (Jul., 1988).

Tait, J.F. et al., "Placental Anticoagulant Proteins: Isolation and Comparative Characterization of Four Members of the Lipocortin Family", *Biochemistry* 27(17):6268–6276 (Aug. 23, 1988).

Tait, J.F. et al., "Phospholipid Binding Properties of the Human Placental Anticoagulant Protein–I, a Member of the Lipocortin Family", *J. Biol. Chem.* 264(14):7944–7949 (May 15, 1989).

Thiagarajan and Tait, "Binding of Annexin V/Placental Anticoagulant Protein I to Platelets", *J. Biol. Chem.* 265:17420–17423 (Oct. 15,1990).

International Search Report for the Related International Application No. PCT/EP 90/02257.

Derwent Abstract for German Patent Application Publications No. DE 3810331, Reference AL1.

Derwent Abstract for European Patent Application Publication No. EP 0 181 465, Reference AP1.

Derwent Abstract for European Patent Application Publication No. EP 0 293 567, Dec. 7, 1988.

Derwent Abstract for European Patent Application Publication No. EP 0 318 703, Jun. 7, 1989.

Derwent Abstract for European Patent Application Publication No. EP 0 409 053, Jan. 23, 1991.

Zubay, "Biochemistry" pp. 169 & 171 (1983) Brown Publishers, Dubuque, Iowa.

*Primary Examiner*—Cecilia J. Tsang
*Assistant Examiner*—Patrick R. Delaney
*Attorney, Agent, or Firm*—Sterne, Kessler, Goldstein & Fox P.L.L.C.

[57] ABSTRACT

Detectably labelled annexines and compositions thereof are disclosed. Also disclosed are methods for diagnosing a disruption or activation of the hemostatic system or a prothrombotic state in an individual suspected of having a hemostatic disorder, by contacting the blood of said individual with an annexine, and detecting whether an annexine-platelet complex is formed.

15 Claims, 5 Drawing Sheets

USE OF AN ANTICOAGULANT AS A DIAGNOSTIC AGENT

CROSS REFERENCE TO RELATED APPLICATIONS

The present application is a division of Appl. Ser. No. 08/183,788, now U.S. Pat. No. 5,627,036, filed Jan. 21, 1994, which is a continuation of Appl. Ser. No. 07/904,366, filed Jun. 26, 1992, abandoned, which is a continuation-in-part of Appl. Ser. No. 07/862,572; filed Jun. 26, 1992, abandoned, the contents of each of which are fully incorporated by reference herein.

FIELD OF THE INVENTION

The present invention is in the field of medicinal chemistry. In particular, the present invention relates to agents, particularly annexines, which are labelled with a detectable substance and the use thereof for diagnostic purposes.

BACKGROUND OF THE INVENTION

Blood consists of special unbound cells dispersed in a plasma medium. The contents of the cell are separated from the surrounding plasma by so-called plasma membranes. These membranes are made up of phospholipids in the form of a double layer and associated proteins which partially penetrate this double layer or protrude from it.

The various phospholipids are not randomly distributed over the outer and inner shell of the double layer but are held by the cell in an asymmetric configuration (Op den Kamp, J. A., *F Ann. Rev. Biochem.* 48:47–71 (1979); Zwaal, R. F. A., *Biochim. Biophys. Acta* 515:163–205 (1978)). Whereas phosphatidyl choline (PC) and sphingomyelin (SPH) are the dominating species of the outer shell, phosphatidyl serine (PS), phosphatidyl ethanolamine (PE) and phosphatidyl inositol (PI) are located predominantly in the inner coat, facing the cytosol. This energy-consuming state of asymmetry is of exceptional physiological importance. PC and SPH are the most inert species of the phospholipid family and in stark contrast to the other species show exceptionally neutral behavior in the presence of the plasma components. This reactive inertia of the outer coat relative to the plasma proteins is the absolute prerequisite for ensuring that the blood remains liquid. Special plasma proteins which belong to the coagulation cascade, namely the so-called coagulation factors, are in fact able to convert liquid blood into a solid state when they are activated (Jackson & Nemerson, *Ann. Rev. Biochem.* 49:765–811 (1980)). These coagulation factors can be activated by phospholipids such as phosphatidyl serine.

In many cases, e.g. after injury to a blood vessel, it is necessary, not to mention crucial to survival, for the coagulation factors to be activated. In such a situation, a special blood cell, called the platelet, can give up its membrane asymmetry by activation mechanisms which transport phosphatidyl serine to the outer coat, where it aids the activation of the coagulation factors (Bevers, E. M., el al., *Biochim. Biophys. Acta* 736:57–66 (1983)).

This systematic change in the pbospholipid composition of the outer coat of the platelet plasma membrane is of major physiological importance in hemostasis, as indicated for example by the Scott syndrome (Rosing, J., et al, *Blood* 65:1557–1561 (1985)).

However, physiology also includes pathology; thus, the homoeostasis of the blood may in some cases slip into a pathological state, as occurs in arterial, coronary and venous thrombosis.

These hemostatic disorders are usually idiopathic and make it impossible for doctors to predict their occurrence and develop preventive treatment.

SUMMARY OF THE INVENTION

The present invention relates to an anticoagulant polypeptide from the family of the annexines, preferably vascular anticoagulant protein (VAC) which has a detectable label.

The present invention also relates to an anticoagulant polypeptide which is detectably labelled with a fluorescent compound, preferably fluorescein isothiocyanate; a radioisotope of a halogen, technetium, lead, mercury, thallium or indium, preferably $^{131}$I or $^{125}$I, or a paramagnetic contrast agent.

The present invention also relates to an anticoagulant polypeptide as described above for distinguishing phosphatidyl serine from phosphatidyl choline.

The present invention also relates to an anticoagulant polypeptide as described above for use as a diagnostic agent.

The present invention also relates to a process for locating the starting point for the activation of the hemostatic system, in which a) a detectable labelled anticoagulant polypeptide or agent, selected from the family of annexines, preferably VAC, is administered to the system, preferably by intraarterial or intravenous route and b) after an incubation period, the distribution of said polypeptide is observed, either extracorporally with a gamma-scintillation camera or by magnetic resonance measurement.

The present invention also relates to a process for diagnosing the prothrombotic state, in which a) the blood to be examined is mixed extracorporally with an anticoagulant polypeptide or agent from the family of annexines, preferably VAC which has a detectable marker and b) the labelling associated with specific cell types is analyzed.

An agent which besides an anticoagulant polypeptide from the family of the annexines, preferably VAC which has a detectable marker, contains additionally an adjuvant such as, for example, a physiological solution of sodium chloride, polyoxyethylene sorbitan monooleate (TWEEN 80) arginine and/or phosphate buffer, an anticoagulant, preferably heparin, which does not reduce the plasma calcium concentration optionally being used.

The present invention also relates to a kit for the diagnostic detection of the prothrombotic state or the starting point of activation of the hemostatic system and/or a thrombus containing an agent or an anticoagulant polypeptide of the invention which is capable of distinguishing phosphatidyl serine from phosphatidyl choline.

The present invention also relates to the use of an anticoagulant polypeptide or agent of the invention for distinguishing phosphatidyl serine from phosphatidyl choline.

The present invention also relates to the use of an anticoagulant polypeptide or agent of the invention for the diagnosis of the prothrombotic state or the starting point of disorder of the hemostatic system or the thrombus.

DESCRIPTION OF THE PREFERRED EMBODIMENTS

The aim of the present invention was to provide agents which would help in the early recognition of hemostatic disorders.

Unlike the development of the symptoms, the development of the disorders usually occurs slowly. During this phase of symptomless progression, known as the prothrombotic state, continuous activation of the coagulation system is occurring locally. Connected with this local activation there is, in the periphery, an occurrence of platelets which are at an early stage of activation. These platelets have already begun to change the phospholipid composition of their outer plasma membrane coat. Phosphatidyl serine is present in the outer coat. Agents which diagnose this so-called protlirombotic state are, therefore, of extremely great clinical importance.

A further object of the invention was to provide adjuvants which are capable of specifically distinguishing phosphatidyl serine from phosphatidyl choline.

In addition to the occurrence of weakly activated platelets in the periphery, fully activated platelets will accumulate anywhere where the wall of the blood vessel is in a pathological condition. This location can be regarded as the trigger for the activation of the hemostatic system. Locating this pathological site and the thrombus forming at this point would be of major therapeutic value.

A further aim of the invention was therefore to provide an agent which allows for the localization of the starting point of the activation of the hemostatic system and/or a thrombus.

The blood coagulation mechanism constitutes a cascade of enzymatic reactions at the end of which is the formation of thrombin which finally converts fibrinogen into fibrin. Various procoagulant reactions such as, for example, the activation of prothrombin by factors Xa and Va are catalyzed by phospholipid surfaces to which the clotting factors bind.

The proteins which bind to phospholipids and interfere with processes dependent on phospholipid surfaces constitute a family which are $Ca^{2+}$-dependent in their binding to phospholipids. This family, also known as the annexines, includes lipocortin I, calpactin I, protein II, lipocortin III, p67-calelectrin, the vascular anticoagulant protein (VAC), IBC, PAP, PAPI, PP4, endonexin II and lipocortin V. Methods for the preparation of annexines are taught by Crompton, M. R. et al., Cell 35:1–3 (1988), Tait, J. et al, Biochem. 27:6268–6276 (1988), Zaetzel, M. A. et al., J.Biol.Chem. 264:14463–14470 (1989), Funakoski, T. et al., Biochem. 26:8087–92 (1987), Giesow, M. J. el al., FEBS 203:99–103 (1986), Giesow, M. J. et al., Biochem Soc. Trans. 25:800–902 (1987), U.S. Pat. Nos. 4,937,324, 4,736,018, and 4,507,229, International Application WO88/05659, and European Application Nos. 0 181 465, 0 293 567, 0 318 703 and 0 279 459, the disclosures of which are fully incorporated by reference herein.

The structural features common to the annexines are presumably the basis for their similar $Ca^{2+}$ and phospholipid-binding properties. Although this general property applies to all annexines, there is clear individuality with regard to their affinity for $Ca^{2+}$ and the various types of phospholipid.

The physiological functions of the annexines relate to membrane-associated processes. The basic mechanism of the anticoagulant effect of VAC was recognized as an inhibition of the catalytic capacity of the phospholipids by the binding of VAC to their surface, thereby preventing the formation of the coagulation-promoting complex on their surface.

Studies of binding have shown that VAC associates reversibly with procoagulatory phospholipids in calcium-dependent manner.

Other bivalent cations from the series $Cd^{2+}$, $Zn^{2+}$, $Mn^{2+}$ and $Co^{2+}$ also have a positive effect on association, but not to the same extent as $Ca^{2+}$.

Furthermore, it has surprisingly been found that VAC absorption on phospholipids is positively influenced to an exceptional degree in the presence of $Ca^{2+}$ and $Zn^{2+}$ ions.

Surprisingly, it has been found that, at plasma-alcium concentrations, VAC binds to phosphatidyl serine but not to phosphatidyl choline and sphingomyelin. VAC will therefore specifically recognize and bind peripheral platelets with PS in their outer membrane coat. Furthermore, VAC will also specifically recognize those locations in the vascular system which are presenting PS to the blood.

This differentiation among phospholipids makes VAC, like the other annexines, an ideal reagent for achieving early recognition of the prothrombotic state as described above.

By means of the present invention it is, surprisingly, possible for the first time to recognize the prothrombotic state of the vascular system. This diagnosis is made possible by the specificity of the agents of the present invention which are capable of recognizing the prothrombotic state of the platelets, which is different from the normal state. Since the prothrombotic state differs from the normal state of the platelets in that the outer coat of only the prothrombotic platelet shows phosphatidyl serine, this principle can be exploited according to the invention by any agent capable of specifically distinguishing phosphatidyl serine from phosphatidyl choline. The agents which may be used according to the invention are characterized by their specificity for phosphatidyl serine, which can be determined by the binding tests described in the specification.

By making use of this specificity of the agents according to the invention it is also possible to locate the starting point for the activation of the hemostatic system and/or the thrombus.

Consequently, the present invention provides, for the first time, agents which make it possible to initiate suitable therapeutic measures by providing for the early diagnosis of a state which might possibly develop into a health-threatening condition.

Preferred agents according to the invention are the anticoagulant polypeptides, provided that they have the necessary specificity for the phospholipid phosphatidyl serine. The family of the annexines, particularly VAC, is particularly preferred.

In order to be able to use the agents according to the invention, particularly VAC or the other annexines as a diagnostic agent, they are detectably labelled in a manner known per se. There are many different labels and methods of labeling known to those of ordinary skill in the art. Examples of the types of labels which can be used in the present invention include, but are not limited to, enzymes, radioisotopes, dyes, fluorescent compounds, chemiluminescent compounds, bioluminescent compounds and metal chelates. Those of ordinary skill in the art will know of other suitable labels for binding to the agents of the invention, or will be able to ascertain the same by the use of routine experimentation. The binding of these labels to the annexines can be accomplished using standard techniques commonly known to those of ordinary skill in the art.

One of the ways in which the annexines can be detectably labeled is by linking the same to an enzyme. This enzyme, in turn, when later exposed to its substrate, will react with the substrate in such a manner as to produce a chemical moiety which can be detected as, for example, by spectrophotometric, fluorometric or by visual means. Enzymes which can be used to detectably label annexines include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetyl-choline esterase.

The annexines may also labeled with a radioactive isotope which can be determined by such means as the use of a gamma counter or a scintillation counter or by autoradiography. Isotopes which are particularly useful for the purpose of the present invention include: $^3$H, $^{125}$I, $^{131}$I, $^{32}$P, $^{35}$S, $^{14}$C or the radioisotopes of lead, mercury, thallium, technetium or indium ($^{203}$Pb, $^{198}$Hg, $^{201}$Tl, $^{99m}$Tc, $^{111}$In).

It is also possible to label the annexines with a fluorescent compound. When the fluorescently labeled annexine is exposed to light of the proper wave length, its presence can then be detected due to the fluorescence of the dye. Among the most commonly used fluorescent labelling compounds are fluorescein isothiocyanate, rhodamine, phycoerythrin, phycocyanin, allophycocyanin, o-phthaldehyde and fluorescamine. Fluorescein isothiocyanate (Serva) may be used for labelling VAC in a manner known per se (Reisher & Orr, *Anal. Biochem.* 26:178–179 (1968)).

The annexines can also be detectably labeled using fluorescent emitting metals such as $^{152}$Eu, or others of the lanthanide series. These metals can be attached to the agents of the present invention using such metal chelating groups as diethylenetriaminepentaacetic acid (DTPA) or ethylenediamine-tetraacetic acid (EDTA).

Labelling is also possible by means of a paramagnetic contrast agent which is detectable in a MRI (magnetic resonance imaging) system. It is possible to use gadolinium, cobalt, nickel, manganese or iron complexes by means of which conjugates may be provided as diagnostic agents which are detectable in a MRI system. A strong magnetic field is used in such systems in order to adjust the nuclear spin vectors of the atoms in the organism. Then the field is destroyed which causes the nuclei to return to their initial state. This process is observed and recorded.

The annexines also can be detectably labeled by coupling them to a chemiluminescent compound. The presence of the chemiluminescent-tagged annexine is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the annexines. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Another technique which may also result in greater sensitivity when used in conjunction with the present invention consists of coupling the annexine to low molecular weight haptens. The haptens can then be specifically detected by means of a second reaction. For example, it is common to use such haptens as biotin (reacting with avidin) or dinitrophenyl, pyridoxal and fluorescamine (reacting with specific anti-hapten antibodies) in this manner. Amplification strategies may be readily applied to these and other labels.

For the purposes of the present invention, the phosphatidyl serine which is quantitated by this assay may be present in blood or may be present in the blood vessels. In this latter situation, the phosphatidyl serine is detected in vivo as an indication of the presence of a thrombus or the activation of the hemostatic system.

The detectably labelled annexines of the present invention are ideally suited for the preparation of a kit. Such a kit may comprise a carrier means being compartmentalized to receive in close confinement therein one or more container means such as vials, tubes and the like, each of said container means comprising the separate elements of the assay. For example, there may be a container means containing a detectably labelled annexine, and further container means containing, for example, standard serial dilutions of phosphatidyl serine in solution. The standard solutions of phosphatidyl serine may be used to prepare a standard curve with the concentration of phosphatidyl serine plotted on the abscissa and the detection signal on the ordinate. The results obtained from a biologic sample such as blood may be interpolated from such a plot to give the concentration of phosphatidyl serine and, thus, an indication of whether the hemostatic system of the individual has been activated.

In carrying out the method for detecting the activation of the hemostatic system, the method comprises:

A. contacting a detectably labeled annexine with the blood of an individual suspected of having a hemostatic disorder;

B. incubating the mixture obtained in step (A) for a time sufficient to allow the binding of said annexine to phosphatidyl serine present on the surface of blood cells; and C. determining the distribution of said detectably labelled annexine on the surface of blood cells and, thereby, the activation of the hemostatic system.

The anticoagulant polypeptides thus provided with a detectable marker may be administered by the intraarterial or intravenous route. The detectably labelled annexines are administered in an amount sufficient to allow for the subsequent measurement of the label after a sufficient incubation period.

In order to diagnose a prothrombotic state, the polypeptide or agent labelled according to the invention is added extracorporally to the blood to be examined, optionally in the presence of a further anticoagulant which does not decrease the plasma calcium concentration such as, for example, heparin, and then the labelling associated with specific types of cells is analyzed.

The detectably labelled annexines according to the invention may be employed as part of a pharmaceutical composition for intravenous or intraarterial administration. For example, the annexine may be combined with blood-isotonic aqueous solution or with adjuvants. Adjuvants may, for example, include TWEEN 80, arginine, phosphate buffers and physiologically compatible preservatives. Other substances are well known to those of ordinary skill may also be used. Methods for preparing and administering such pharmaceutical compositions are taught in Remington's *Pharmaceutical Sciences*, Mack Publishing Co., Easton, Pa., Osol (ed.) (1980).

The radioactive labelling is carried out using, for example, the known iodogen method (Fraker & Speck, *Biochem. Biophys. Res. Comm.* 80:849–857 (1978)) or the conventional chloramine-T method. In view of its half-life of 8 days, $^{131}$I is recommended for in vivo diagnosis. The radioactively labelled agent is taken up in blood-isotonic aqueous solution. After sterile filtration it is injected. The whole body scintigraphs are taken with a gamma camera, e.g. for $^{131}$I, 1, 2, 4 and 7 days after the injection.

As well as the native forms of the annexines it is also possible to use altered forms for the purposes of the invention. Reference is made in particular to the mutants described in EPA 0 293 567, the disclosure of which is fully incorporated by reference herein. Furthermore, the fragments or chemically modified derivatives of the annexines may also be used which are specific to the phospholipids phosphatidyl serine/phosphatidyl choline and are therefore capable of recognizing the prothrombotic state of the platelets involved.

Preferably, the proteins with VAC activity may be prepared by genetic engineering. According to European Patent Application Publication No. 0 293 567, this was achieved by clarifying the amino acid sequence of parts of the proteins with VAC activity which were isolated from strongly vascularized tissue and highly purified according to European Patent Application Publication no. 0 181 465 (which is fully incorporated by reference herein) by preparing synthetic DNA probes using these sequences and investigating cDNA libraries therewith. After isolation of cDNA hybridizing with the probes, sequence determination and suitable manipulation, this cDNA was expressed in suitable host systems, for example in bacteria, yeast or mammalian cells.

One of the purified proteins was enzymatically cleaved with trypsin. The peptides formed were separated and selected fragments were sequenced. However, the sequence of the N-terminus defied direct analysis since the first amino acid was blocked.

A suitable DNA probe can be produced basically by three methods. Briefly, if a fairly long section of the protein, roughly 30 or more amino acids long, is known, it is possible to establish a fairly probable sequence for the corresponding mRNA section, taking into account the codons preferably used in mammals. A probe of this kind is, in the worst instance, about 66% homologous with the actual sequence. This is the reason why the probe has to be relatively long so as to be able to hybridize under non-stringent conditions.

The second possibility is to synthesize all the conceivable variations of oligonucleotides for a short peptide section, roughly six to seven amino acids long. If such complex mixtures are used in the investigation of cDNA libraries, a relatively large number of "false" positive-reacting clones may be isolated. Furthermore, the hybridization signal may be very weak, since the single oligonucleotide which fits perfectly will make up only a small part of the total mixture.

The third method admittedly does not get around the variability of an oligonucleotide probe but, by the choice of a special nucleoside triphosphate (NTP) it does ensure that all the molecules of the probe can bind to the cDNA sought (or also to "false" cDNA). Thus, oligonucleotides 23 bases long corresponding to the tryptic peptide [P30/I] have been synthesized using inosine triphosphate.

VAC proteins may be isolated from strongly vascularized tissue. The ideal tissues are umbilical cord vessels or placenta. Therefore, and since it is known that almost all genes are expressed in the placenta, by contrast with other special tissues, the above-mentioned DNA probes may be used to investigate a placental cDNA library which had been prepared from placental tissue in a manner known per se, to search for cDNA molecules which code for VAC proteins. For further details regarding the preparation of annexines from natural or recombinant sources, reference is made to European Patent Application Ser. Nos. 0 181 465 and 0 293 567, both of which are fully incorporated by reference herein.

It is intended that any animal may be treated with the pharmaceutical compositions of the present invention. Preferably, such animal is a human, however, the invention is not intended to be so limited. Thus, a human may be screened for a hemostatic disorder.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Materials and Methods

VAC is produced analogously to either EPA 0 181 465 or EPA 0 293 567, which are fully incorporated by reference herein. The following experiments were carried out with VAC-α, but the results can also be applied to the other annexines, particularly VACβ.

Lipids

Dioleoyl-phosphatidyl choline (DOPC, No. P-1013), Dioleoyl-phosphatidyl ethanolamine (DOPE, No. P-0510), Cardiolipin (CL, No. C-5646), Dioleoyl-phosphatidyl glycerol (DOPG, No. P-9664), Phosphatidyl inositol (PI, No. P-0639), Dioleoyl-phosphatidic acid (DOPA, No. P-2767), Stearylamine (SA, S-6755) and egg yolk sphingomyelin (S-0756) were obtained from Sigma Chemical Co.

The purity of DOPC and DOPE was tested by thin layer chromatography. Dioleoyl-phosphatidyl serine (DOPS) was produced by conversion of DOPC according to Confurius & Zwaal (*Biochim. Biophys. Acta* 488:42 (1977)). $^{14}$C-labelled DOPS (specific activity 100,000 dpm/µg) was obtained from Amersham.

Preparation of the Phospholipid Double Layers on Silicon Plates

Phospholipid double layers were applied using a "Langmuir-film balance" (Lauda type FW-1) as described in Corsel et al. (J. Colloid Interface Sci 111:544–554 (1986)). Hydrophilic silicon plates were treated for 24 hours in 30% chromosulphuric acid and water and stored in 50% ethanol/water. Before use they were thoroughly washed with detergent and water. The film balance was filled with demineralized water and 50 μM $CaCl_2$. 20 μl of a solution containing about 2 g/l of phospholipid in chloroform were applied to this substrate. The DOPS fractions in the double layers were tested with $^{14}$C-labelled DOPS mixed with DOPC. The double layers filled up were removed from the silicon plates with the scintillation detergent (Du Pont Formula 989) and the total radioactivity was measured in a scintillation counter.

Measurement of Binding by Ellipsometry

The adsorption of VAC on the phospholipid double layers was measured by means of an automatic ellipsometer as described previously (Corsel, J. W., et al., J. Colloid Interface Sci. 111:544–554 (1986); Cuypers, P. A., et al., J. Biol. Chem. 258:2426–2431 (1983)).

The binding tests were carried out in a hydrophilic cuvette containing 5 ml of a stirred buffer (0.05 M Tris/HCl; 0.1 M NaCl; pH=7.5; T=20° C.). The divalent cations were added stepwise as chlorides.

At VAC-concentrations of <0.1 μg/ml, the buffer which contained the specific VAC concentration was added continuously in order to create an adequate buffer capacity for VAC.

The refractive index and the thickness d of the adsorbed film were determined from the combined polarizing and analyzing data (McCrackin, F. L., et al., J. Res. Nat. Bur. Stand. Sect. A 67:3–337 (1963)). The quantity Γ of the adsorbed protein layer was determined from the refractive index and the thickness using a modified Lorentz-Lorenz equation [1] (Cuypers, P. A., el al., J. Biol. Chem. 258:2426–2431 (1983); Kop, J. M. M. et al., J. Biol. Chem. 259:13993–13998 (1984)):

$$\Gamma = \frac{3d(n^2 - nb)^2}{[(n^2 + 2)(r(nb^2 + 2) - v(nb^2 - 1))]}; \quad [1]$$

nb is the refractive index of the buffer. The values r=0.254 and v=0.71 were used for the specific molar refractivity and the partial specific volume (Cuypers, P. A., el al., J. Biol. Chem. 258:2426–2431 (1983)).

RESULTS

The Effect of Divalent Cations on the Binding of the VAC to Phospholipids

Figure 1:
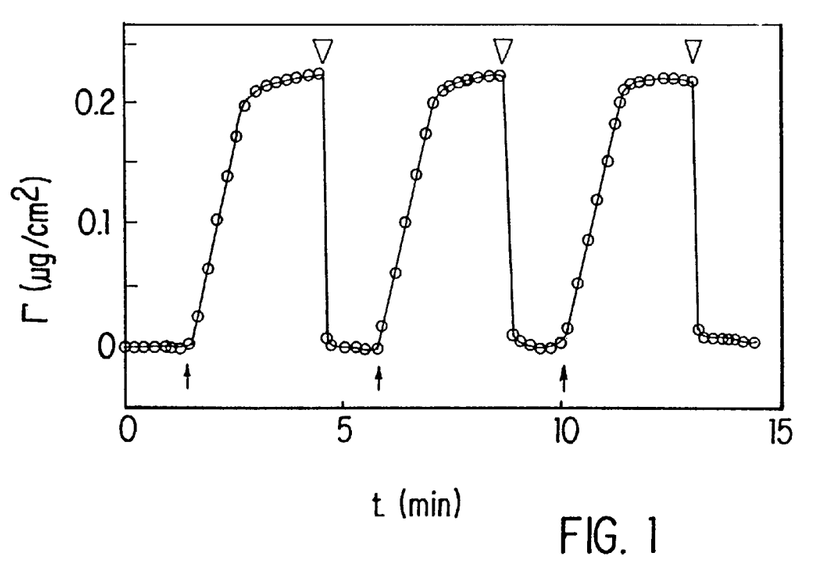
FIG. 1 depicts the alternating adsorption and desorption of VAC on a phospholipid surface, induced by increasing and lowering the $Ca^{2+}$ concentration. The adsorption of VAC (1 μg/ml) on a 20% DOPS/80% DOPC phospholipid double layer. Addition of $Ca^{2+}$ (3,4,6 mM) is indicated by ↑ or ▽.
Figure 2:
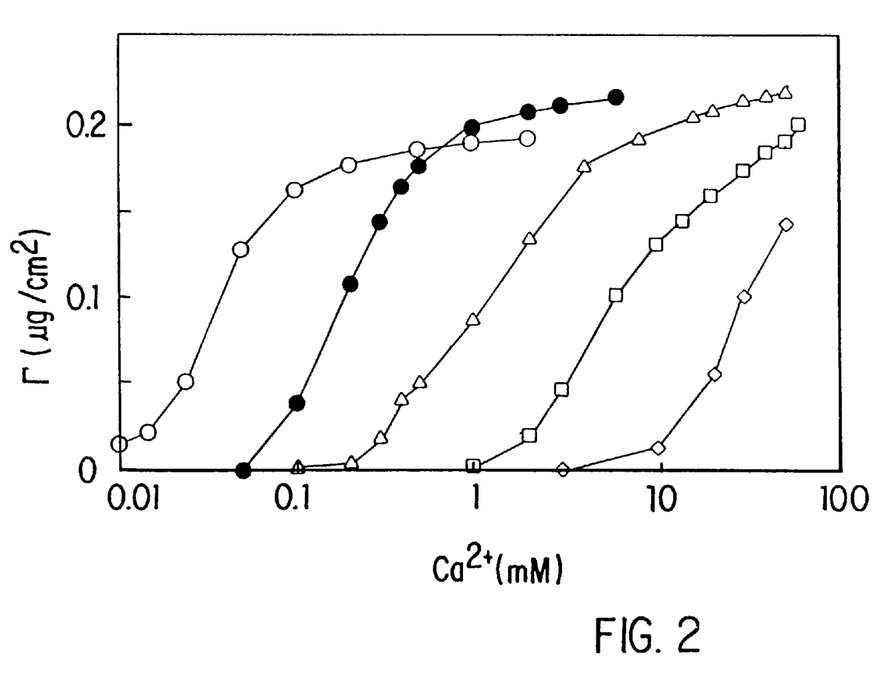
FIG. 2 depicts the influence of the phospholipid composition and $Ca^{2+}$ concentration on the adsorption of VAC on a phospholipid surface. ○100% DOPS; •20% DOPS; Δ5% DOPS; □1% DOPS; 100% DOPC; all the mixtures were supplemented with DOPC. [VAC]=1 μg/ml.
Figure 3:
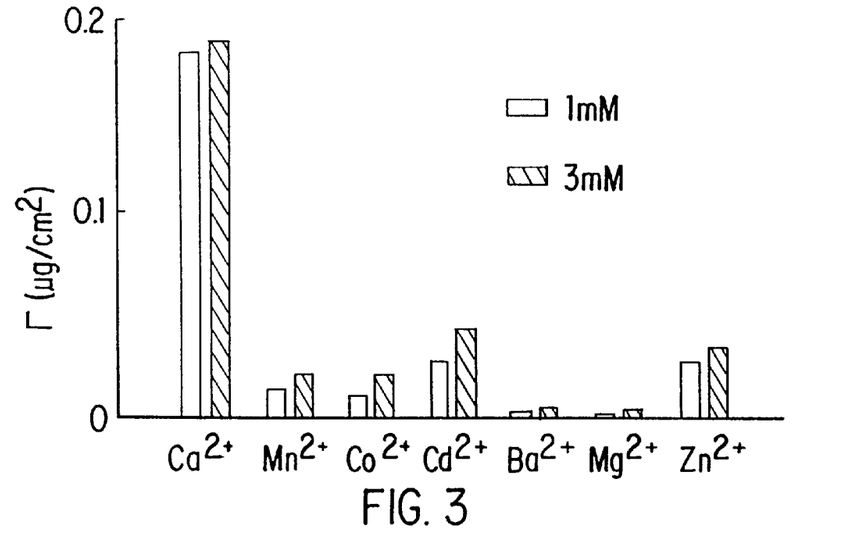
FIG. 3 depicts the effect of bivalent ions on the adsorption of VAC. VAC adsorption on double layers of 20% DOPS and 80% DOPC in the presence of the ions specified (1 or 3 mM). [VAC]=1 μg/ml.
Figure 4:
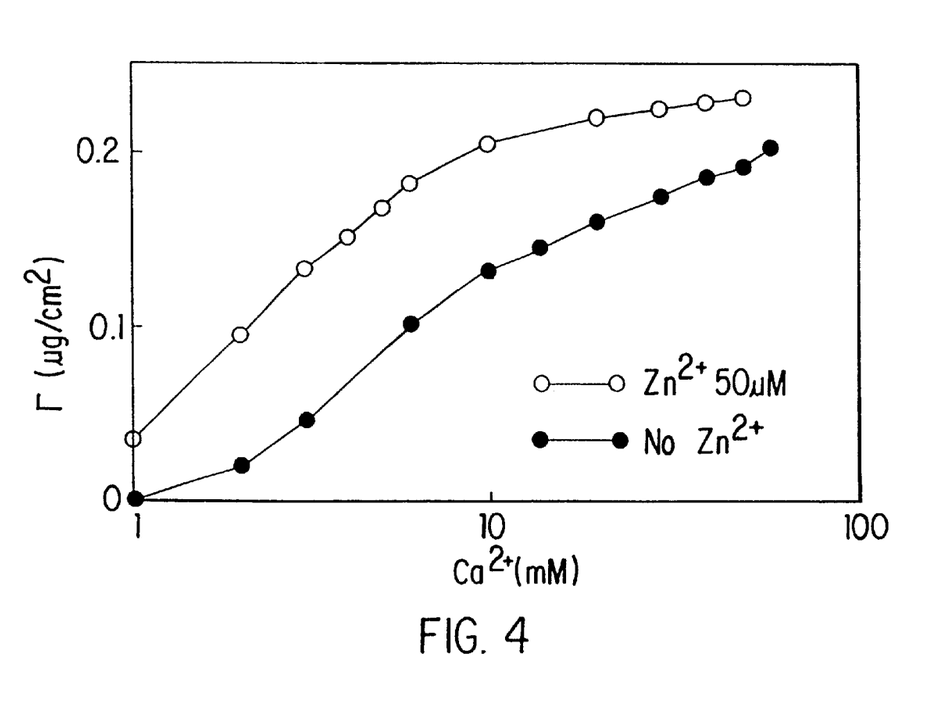
FIG. 4 depicts the synergistic effect of $Zn^{2+}$ on the $Ca^{2+}$-dependent adsorption of VAC on the phospholipid surface. The effect of $Ca^{2+}$ on the VAC adsorption on 1% DOPS and 99% DOPC in the presence of 50 μM $Zn^{2+}$ was measured. [VAC]=1 μg/ml.
Figure 5:
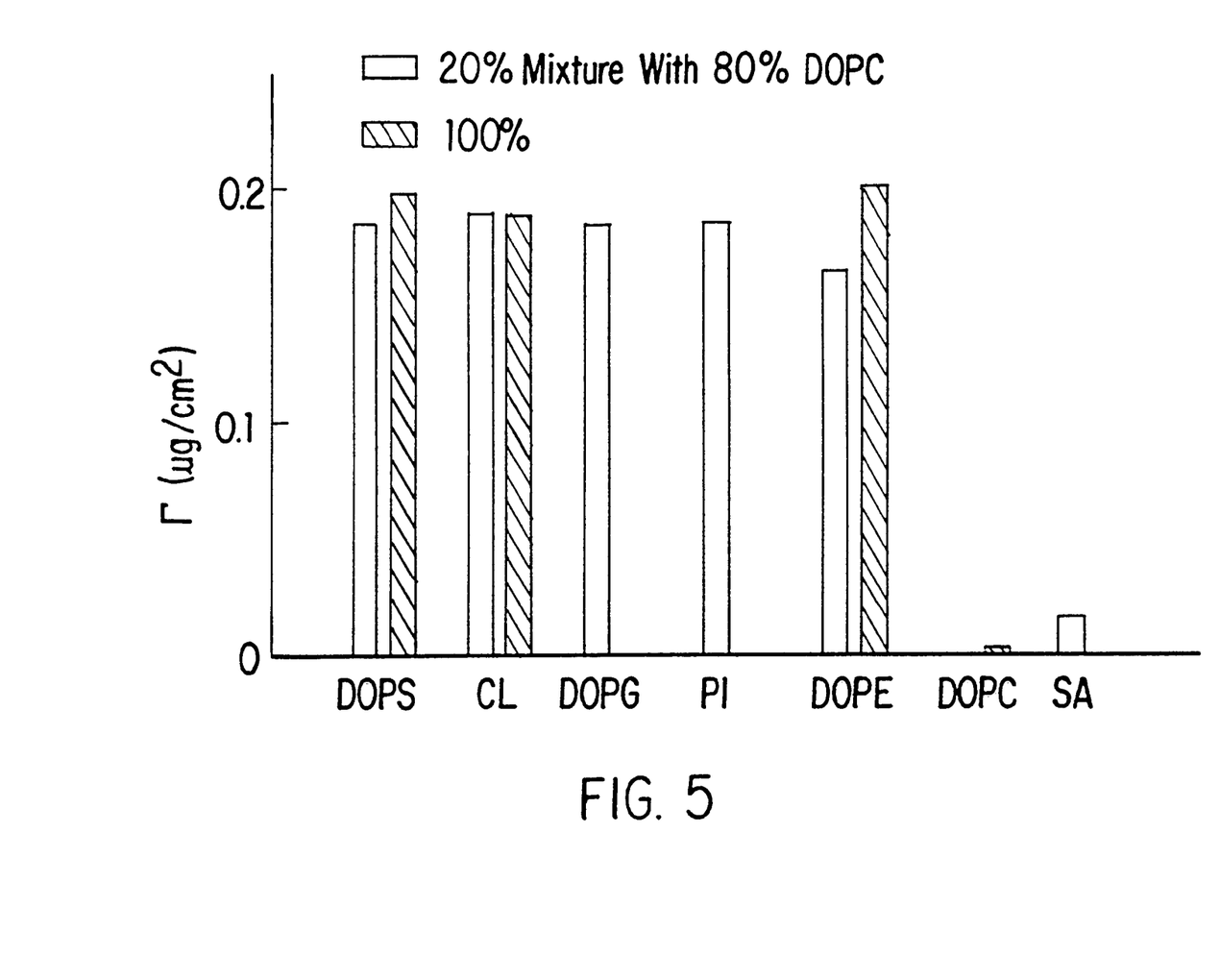
FIG. 5 depicts the adsorption of VAC on phospholipid double layers of varying composition. VAC adsorption on dioleoyl phosphatidyl serine (DOPS), cardiolipin (CL) and dioleoyl phosphatidyl ethanolamine (DOPE), either pure or mixed with 80% dioleoyl phosphatidyl choline (DOPC), on dioleoyl phosphatidyl glycerol (DOPG), phosphatidyl inositol (PI) and stearylamine mixed with 80% DOPC or on pure DOPC. [VAC]=1 μg/ml; $[Ca^{2+}]$=3 mM.
Figure 6:
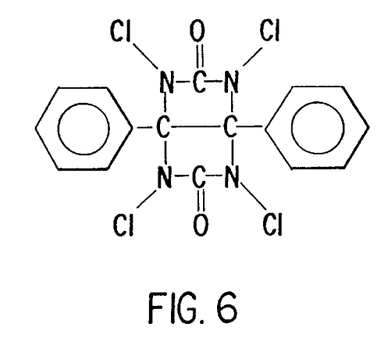
FIG. 6 depicts 1,3,4,6-Tetrachloro-3α-6α-diphenyl-glycoluril (IODO-GEN).

VAC binds to phospholipid membranes consisting of 20% DOPS/80% DOPC, depending on the calcium concentration. The subsequent addition of EDTA resulted in immediate and total desorption (FIG. 1). By varying the free $Ca^{2+}$ concentration it was possible to initiate adsorption several times, without any noticeable change in the quantity adsorbed or the rate of adsorption. Irreversible changes to the VAC molecule or the phospholipid double layers caused by adsorption or desorption are therefore improbable. The binding was also totally reversible when the cuvette was rinsed out with $Ca^{2+}$-free buffer.

The $Ca^{2+}$ dependency of the VAC binding to phospholipids is shown in FIG. 2. The $Ca^{2+}$-dosage-activity curve shows quite clearly a $Ca^{2+}$ concentration at which half the maximum VAC adsorption is achieved: $[Ca^{2+}]_{1/2}$. The $[Ca^{2+}]_{1/2}$ value depends on the composition of the phospholipid surface. With phospholipid surfaces containing 100%, 20%, 5% and 1% DOPS, $[Ca^{2+}]_{1/2}$ values of 36 $\mu$M, 220 $\mu$M, 1.5 mM and 8.6 mM were measured, respectively (Table 1). These results accord particularly well with the $[Ca^{2+}]_{1/2}$ value of 53 $\mu$M, which was measured for the endonexin II (=VAC) binding to equimolar mixtures of PS/PC vesicles (Schlaepfer, D. D., et al., *Proc. Natl. Acad. Sci*. USA 84:6078–6082 (1987)). The maximum quantity of protein adsorbed (Γmax) was independent of the DOPS fraction of the membrane and amounted to approximately 0.217 $\mu g/cm^2$. No adsorption was detected with pure DOPC double layers up to a $Ca^{2+}$ concentration n of 3 mM.

The adsorption of VAC to the phospholipid double layers of different concentrations is shown in FIG. 5. It is shown quite clearly here that virtually no adsorption of VAC is found with pure DOPC double layers. The adsorption of VAC to stearylamide (SA) is also weak.

In experiments with cations other than $Ca^{2+}$, it was found that the binding of VAC to the phospholipids is strongly $Ca^{2+}$-specific (FIG. 3). $Cd^{2+}$, $Zn^{2+}$, $Mn^{2+}$ and $Co^{2+}$ showed little promotion of binding; $Ba^{2+}$ and $Mg^{2+}$ had no influence. This property of the cations can to some extent be correlated with the ion radii thereof.

Zinc Synergism

High concentrations of zinc ions (1 mM) promote VAC-adsorption only to a small extent (FIG. 3); 50 $\mu$M have no effect whatsoever on adsorption. Surprisingly, this concentration does influence binding in the presence of $Ca^{2+}$; there is some synergism. The $[Ca^{2+}]_{1/2}$ value fell from 8.6 to 2.7 mM for double layers having only 1% DOPS ($[Zn^{2+}]$50 $\mu$M) (FIG. 4). 50 $\mu$M $[Zn^{2+}]$is within the normal range of the plasma zinc concentrations.

Diagnostic Methods

1. In vitro diagnosis
   - a) VAC is labelled by methods known per se with the fluorescein group, e.g. with fluorescein isothiocyanate; in this way VAC-FITC is obtained.
   - b) A patient's blood is placed in a plastic test tube containing an anticoagulant which does not reduce the plasma-calcium concentration (e.g. heparin) and VAC-FITC.
   - c) After mixing, the blood cells are analyzed using an FACS (fluorescence activated cell sorter). This analysis determines the intensity of fluorescence, which is associated with specific types of cell.
   - d) The analysis profiles show the quantity of platelets with bound VAC-FITC, i.e. platelets with exposed PS, and therefore the presence of a prothrombotic condition. This health-threatening condition can be recognized early by this method and consequently treated at an early stage.
2. In vivo diagnosis
   - a) VAC is labelled with a short-lived isotope, for example $^{131}$I using methods known per se; $^{131}$I-VAC is obtained.
   - b) $^{131}$I-VAC is administered intravenously to a patient.
   - c) After a certain incubation period the patient is exposed to whole or partial body scintigraphy. The distribution of radioactivity can be observed using a large-field-of-view gamma camera.
   - d) Intravascular sites with $^{131}$I-VAC accumulation mark the point where the thrombosis is progressing. Suitable thrombosis-preventing or thrombosis-alleviating measures can be taken early.

1. Radioactive Labelling

1.1 Preparations

1.1.1. Preparation of a 500 mmol/l sodium phosphate buffer 24.5 g of sodium dihydrogen phosphate monohydrate were dissolved in 1 liter of twice distilled water and added to a solution of 35.5 g of disodium hydrogen phosphate in 1 liter of twice distilled water until a pH of 7.5 was achieved.

1.1.2. Preparation of a 20 mmolal sodium phosphate buffer+150 mmol NaCl (elution buffer)

2.76 g of sodium dihydrogen phosphate monobydrate were dissolved in 1 liter of twice distilled water and added to a solution of 2.84 g of disodium hydrogen phosphate in 1 liter of twice distilled water until a pH of 7.2 was obtained. The elution buffer was prepared by adding 8.77 g NaCl (150 mmol) to 1 liter of the buffer.

1.1.3. Equilibration of the purification column

A PD-10 column (Sephadex G25. Messrs. Pharmacia) was equilibrated with about 30 ml of the elution buffer.

1.1.4. Preparation of the reaction vessel 2 mg of IODO-GEN (molecular mass: 432.09 g/mol) were dissolved in 50 ml of highly pure dichloromethane. 200 $\mu$l of this solution were pipetted into a 1.5 ml Eppendorf container and then the solvent was evaporated off at 37° C. (thermostatic block). In this way 8 $\mu$g ($1.85\times10^{-2}$ mmol) of IODO-GEN were finely distributed over the wall of the reaction vessel.

1.1.5. VAC-α used for labelling

The starting material used was a solution of 50 mg VAC-α in 4 ml of 20 mmol/l sodium phosphate buffer+150 mmolA NaCl, pH 7.2, diluted with 1 ml of twice distilled water. Molecular mass VAC-α: 34000 g/mol.

1.1.6. I-125 used for labelling

Na$^{125}$I made by Dupont, NEN products, with 67.3 MBq (=1.82 mCi) total radioactivity on the date of calibration. The specific activity was 15.9 Ci/mg of iodine=1.98 kCi/mmol ½ I$_2$, corresponding to 0.115 $\mu$g of iodine ($9.2\times10^{-7}$ mmol ½ I$_2$). The active NaI was dissolved in 5.5 $\mu$l of 0.1 mol/l NaOH.

1.2. Iodination

All the work was carried out with removal of the isotope behind leaded glass screens. 20 $\mu$l (=200 $\mu$g) of the solution of VAC-α described in 1.1.5. were transferred into the reaction vessel pretreated with IODO-GEN. This vessel was sealed and shaken for 20 minutes at ambient temperature. Then the reaction solution was applied by means of a pipette to the prepared PD-10 column (see 1.1.3.). The reaction vessel was rinsed again with 500 $\mu$l of the elution buffer (see 1.1.2.) and this solution was also applied to the PD-10 column. The eluate flowing out was discarded.

1.3. Purification

By the application of 0.5 ml aliquots of elution buffer (see 1.1.2) at 2 minute intervals, the VAC-α[$^{125}$I] was separated from the free $^{125}$I/Na $^{125}$I. After 12 fractions, this purification step was complete.

Figure 7:
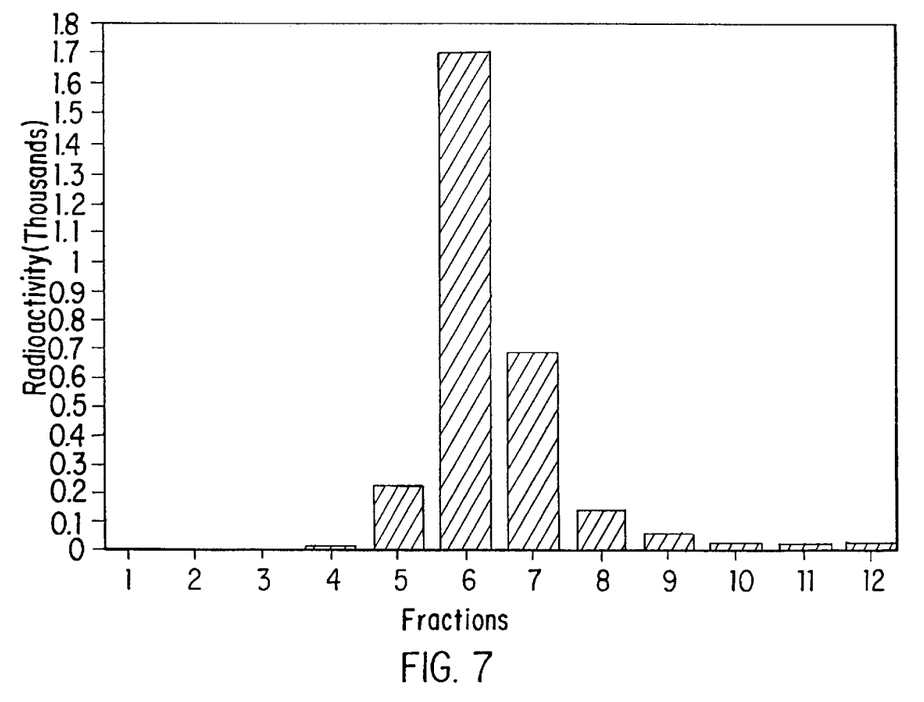
FIG. 7 depicts the distribution of radioactivity in the fractions 1–12.

The relative activity content of the fraction was measured using a laboratory monitor (GMZ) (FIG. 7).

Fractions 6 and 7 were combined, made up to precisely 2.0 ml with elution buffer, divided into 100 $\mu$l portions and frozen at –20° C. The substance was kept available in these portions for analysis and developmental studies.

2. Analytical Methods

2.1. Measurement of Content

In the chromogenic substrate assay a VAC-α content of 71.8 $\mu$g/2.0 ml of solution was measured.

ks2.2. Measurement of Radioactivity 2.2.1. Total radioactivity

After a 100 $\mu$l portion had been thawed, 50 $\mu$l of this [$^{125}$I VAC-α solution was added by pipette to 950 $\mu$l of the inactive VAC-α solution (see 1.1.5.), thoroughly mixed and 50 $\mu$l thereof was placed in an LSC-Counter (Beckman) for measurement. 24.5 MBq (=0.663 mCi)/2.0 ml of total solution.

2.2.2. Specific activity

Measurement of the content and total radioactivity yielded a specific activity of 341.5 MBq/mg=11.61 TBq/mmol (9.23 mCi/mg=313.8 Ci(mmol))

2.2.3. Measurement of the protein-bound radioactivity by TCA precipitation

100 $\mu$l of the VAC-α solution were combined with 50 $\mu$l of 3% BSA solution and 150 $\mu$l of 40% aqueous trichloroacetic acid, shaken thoroughly and left to stand for 60 minutes in a refrigerator. The precipitate formed was removed by centrifuging. Aliquots of the supernatant were measured in an LSC-counter. Result: 99.3% of the radioactivity was precipitable.

2.2.4. Radioactivity yield

Of the 67.3 MBq put in, 24.5 MBq were found in the VAC-α. The activity yield was therefore 36.4%.

2.3 Degree of Modification

From the specific activity and the quantity of inactive VAC-α used, it was calculated that statistically every 6th VAC-α molecule was labelled with a $^{125}$I-atom.

3.4 Identity and Purity

Figure 8:
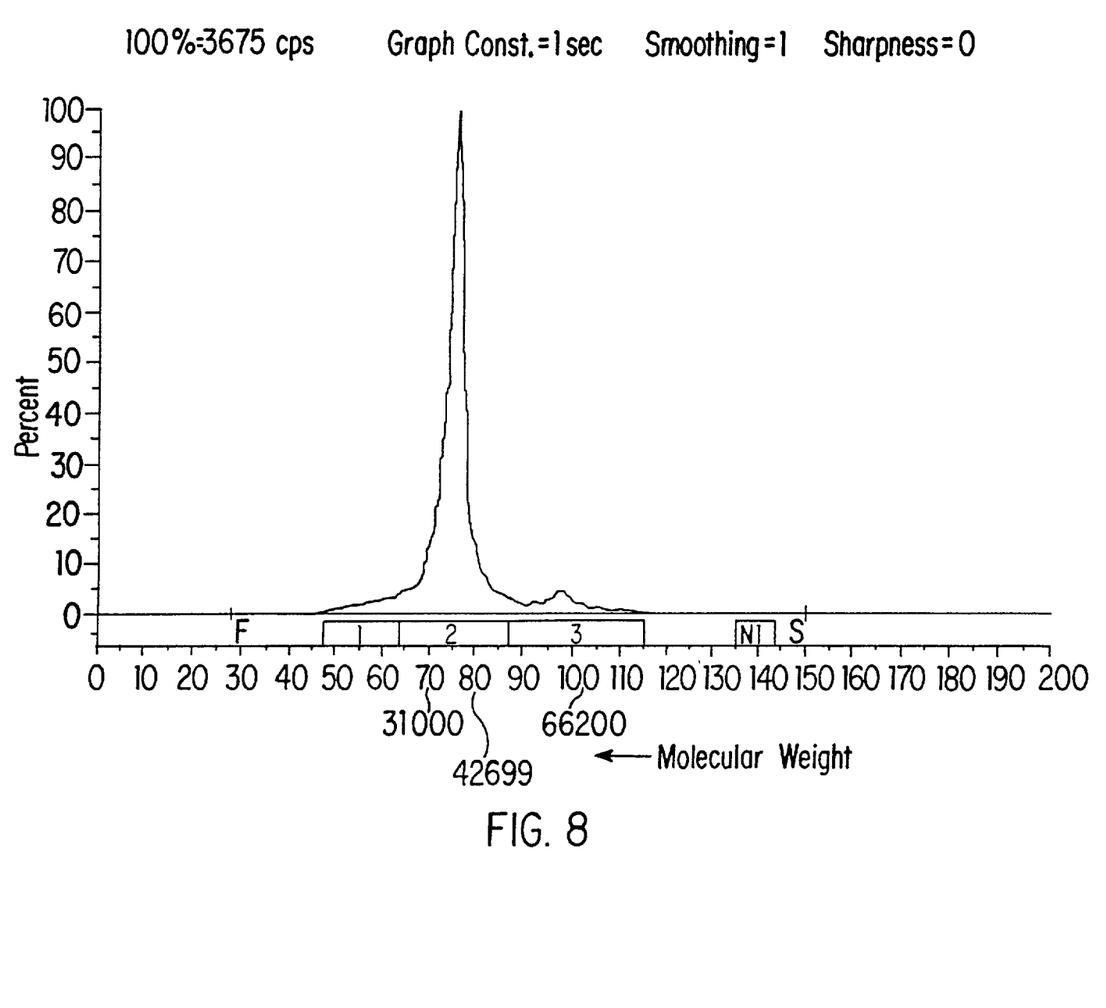
FIG. 8 depicts the distribution of radioactivity under the linear analyzer.

Using the SDS-PAGE (gradient gel 7 to 17%, nonreducing conditions) and subsequent evaluation of the gel by silver staining (Oakley method), autoradiography and detection under the linear analyzer (made by Berthold LB 282, probe LB 2820) (FIG. 8) the substance was investigated by comparison with the VAC-α used. The substances were identical, the proportion of dimeric product was significantly below the limit of 8% tolerated for inactive charges.

TABLE 1

Evaluation of the phospholipid double layers applied to silicon plates

| $^{14}$C-DOPS on film balance % | Quantity of phospholipids (by ellipsometry) $\mu$g/cm$^2$ | Activity DPM | DOPS fraction measured % |
|---|---|---|---|
| 2 | 0.396 | 453 | 1.9 |
| 5 | 0.409 | 1133 | 4.5 |
| 20 | 0.401 | 5006 | 20 |
| 100 | 0.442 | 27174 | 99 |

The calculated mixture was placed on the film balance. The quantity of double layer was measured by ellipsometry and the activity of the $^{14}$C-labelled DOPS was measured using a Beckmann 6S 3801 scintillation counter (s.d.<2%) and corrected by the background radiation (60 DPM). The DOPS fraction in the double layer was calculated using equation 2:

$$\text{Fraction} = \frac{\text{Quantity } (\mu g/cm^2) \times \text{spec. activity}(DPM \cdot \mu g^{-1})}{\text{Activity }(DPM) \times \text{area }(cm^2)}$$

The specific activity of DOPS was 100,000 DPM.$\mu$g$^{-1}$, the area occupied by phospholipids was 0.62 cm$^2$.

TABLE 2

Half the maximum VAC-binding to various phospholipid surfaces

| Lipid (mol %/mol %) | $\Gamma$max ± S.D. ($\mu$g/cm$^2$) | [Ca$^{2+}$]$_{1/2}$ ± S.D. mM |
|---|---|---|
| DOPS (100) | 0.195 ± 0.025 | 0.036 ± 0.013 |
| DOPS/DOPC (20/80) | 0.222 ± 0.014 | 0.22 ± 0.06 |
| DOPS/DOPC (5/95) | 0.229 ± 0.004 | 1.5 ± 0.5 |
| DOPS/DOPC (1/99) | 0.234 ± 0.007 | 8.6 ± 2.5 |
| Cardiolipin/DOPC (20/80) | 0.209 ± 0.011 | 0.039 ± 0.022 |
| DOPG/DOPC (20/80) | 0.212 ± 0.003 | 0.155 ± 0.027 |
| PI/DOPC (20/80) | 0.221 ± 0.005 | 0.47 ± 0.05 |
| DOPA/DOPC (20/80) | 0.207 ± 0.006 | 0.75 ± 0.26 |
| DOPE/DOPC (20/80) | 0.213 ± 0.003 | 0.86 ± 0.21 |
| Sphingomyelin/DOPC (20/80) | 0.225 ± 0.014 | 7 ± 3 |
| DOPC (100) | n.d. | >30 mM |

The maximum VAC-adsorption ($\Gamma$max) on the phospholipid surfaces specified together with the calcium concentration resulting in half the maximum VAC binding Ca$^{2+}$]$_{1/2}$ are given as the averages of at least three different experiments with the corresponding standard deviations. n.d.=not determined.

From the foregoing description, one skilled in the art can easily ascertain the essential characteristics of this invention, and without departing from the spirit and scope thereof, can make various changes and modifications of the invention to adapt it to various usages and conditions, without undue experimentation.

What is claimed is:

1. A detectably labelled annexine which is useful for diagnosing a prothrombic state.

2. A detectably labelled annexine which is useful for detecting the point of activation of the hemostatic system.

3. A detectably labelled annexine which is useful for distinguishing between phosphatidyl serine and phosphatidyl choline.

4. The detectably labelled annexine of any of claims 1, 2, or 3, wherein said annexine is vascular anticoagulant protein (VAC).

5. The detectably labelled annexine of claim 1, wherein said label is a fluorescent molecule or radiolabel.

6. The detectably labelled annexine of claim 1, wherein said radiolabel is $^{125}$I, $^{123}$I, $^{131}$I, $^{111}$In, $^{99m}$Tc, $^{203}$Pb, $^{198}$Hg or $^{201}$Tl.

7. The detectable labelled annexine of claim 1, wherein said annexine is VAC labelled with $^{125}$I.

8. A pharmaceutical composition comprising the detectably labelled annexine of claim 1 and an adjuvant.

9. The pharmaceutical composition according to claim 8, wherein the adjuvant is selected from at least one of the group consisting of physiological saline solution, polyoxyethylene sorbitan monooleate, arginine and phosphate buffer.

10. The pharmaceutical composition according to claim 8, further comprising an anticoagulant which does not reduce the plasma calcium concentration.

11. The pharmaceutical composition according to claim 10, wherein said anticoagulant is heparin.

12. The detectably labelled annexine of claim 4, wherein said label is a fluorescent molecule or radiolabel.

13. The detectably labelled annexine of either of claims 2 or 3, wherein said label is a fluorescent molecule or radiolabel.

14. The detectably labelled annexine of claim 4, wherein said annexine is VAC labelled with $^{125}$I.

15. The detectably labelled annexine of any one of claims 5, 6, 2 or 3, wherein said annexine is VAC labelled with $^{125}$I.

* * * * *